(12) United States Patent
Herbst et al.

(10) Patent No.: US 10,865,401 B2
(45) Date of Patent: Dec. 15, 2020

(54) PROTEASE WITH IMPROVED WASHING PERFORMANCE

(71) Applicant: Henkel AG & Co. KGaA, Duesseldorf (DE)

(72) Inventors: Daniela Herbst, Duesseldorf (DE); Timothy O'Connell, Landsberg am Lech (DE); Nina Mussmann, Willich (DE); Brian Laufs, Juechen (DE); Ayhan Aydemir, Duesseldorf (DE); Renee Charlott Eichstaedt, Cologne (DE); Inken Prueser, Dueseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 122 days.

(21) Appl. No.: 16/091,666

(22) PCT Filed: Apr. 4, 2017

(86) PCT No.: PCT/EP2017/057907
§ 371 (c)(1),
(2) Date: Oct. 5, 2018

(87) PCT Pub. No.: WO2017/174536
PCT Pub. Date: Oct. 12, 2017

(65) Prior Publication Data
US 2019/0127719 A1 May 2, 2019

(30) Foreign Application Priority Data
Apr. 6, 2016 (DE) .................. 10 2016 205 670

(51) Int. Cl.
*C12N 9/54* (2006.01)
*C11D 3/386* (2006.01)

(52) U.S. Cl.
CPC ............... *C12N 9/54* (2013.01); *C11D 3/386* (2013.01); *C11D 3/38618* (2013.01)

(58) Field of Classification Search
CPC ..................................................... C12N 9/48
See application file for complete search history.

(56) References Cited

FOREIGN PATENT DOCUMENTS

| WO | 2009149144 A2 | 12/2009 | |
|---|---|---|---|
| WO | 2009149200 A2 | 12/2009 | |
| WO | 2010056653 A2 | 5/2010 | |
| WO | 2011/072099 * | 6/2011 | ............... C12N 9/64 |
| WO | 2011072099 A2 | 6/2011 | |

OTHER PUBLICATIONS

USPTO in house BLAST alignment of SID1 with the variant of SID 2 of Basler, 2011 WO 2011/072099 as per claim 52b.*
Paul Carter, Lars Abrahmsen, and James A. Wells; Probing the mechanism and improving the rate of substrate-assisted catalysis in subtilisin BPN'; Biochemistry 1991 30 (25), 6142-6148; Jun. 25, 1991.

* cited by examiner

*Primary Examiner* — Sheridan Swope
(74) *Attorney, Agent, or Firm* — Lorenz & Kopf, LLP

(57) ABSTRACT

The present disclosure relates to proteases comprising an amino acid sequence which has at least about 70% sequence identity to the amino acid sequence indicated in SEQ ID NO. 1, over the entire length thereof, and in which the amino acids in the positions corresponding to positions 24, 33, 53, 78, 101, 128 and 217 according to SEQ ID NO. 1 are substituted at 24G, 33T, 53G, 78N, 101N, 128A and 217Q, and to the production and use thereof. Said type of proteases have a very good cleaning performance compared to reference proteases.

1 Claim, No Drawings
Specification includes a Sequence Listing.

SEQUENCE LISTING

<160> NUMBER OF SEQ ID NOS: 2

<210> SEQ ID NO 1
<211> LENGTH: 275
<212> TYPE: PRT
<213> ORGANISM: Bacillus amyloliquefaciens

<400> SEQUENCE: 1

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 2
<211> LENGTH: 275
<212> TYPE: PRT
<213> ORGANISM: Artificial Sequence
<220> FEATURE:
<223> OTHER INFORMATION: Mutant of Bacillus amyloliquefaciens protease

```
<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Gly Asn Val Lys Val Ala Val Ile Asp
            20                  25                  30

Thr Gly Ile Asp Ser Ser His Pro Asp Leu Lys Val Ala Gly Gly Ala
        35                  40                  45

Ser Met Val Pro Gly Glu Thr Asn Pro Phe Gln Asp Asn Asn Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Gly Ala Asp Gly Asn Gly Gln Tyr Ser Trp Ile Ile Asn Gly Ile Glu
            100                 105                 110

Trp Ala Ile Ala Asn Asn Met Asp Val Ile Asn Met Ser Leu Gly Ala
            115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
            165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
    195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
            245                 250                 255

Leu Gly Asp Ser Phe Tyr Tyr Gly Lys Gly Leu Ile Asn Val Gln Ala
            260                 265                 270

Ala Ala Gln
        275
```

PROTEASE WITH IMPROVED WASHING PERFORMANCE

CROSS-REFERENCE TO RELATED APPLICATION

This application is a U.S. National-Stage entry under 35 U.S.C. § 371 based on International Application No PCT/EP2017/057907, filed Apr. 4, 2017 which was published under PCT Article 21(2) and which claims priority to German Application No. 10 2016 205 670.0, filed Apr. 6, 2016, which are all hereby incorporated in their entirety by reference.

TECHNICAL FIELD

The present disclosure lies in the field of enzyme technology. The present disclosure relates to proteases from *Bacillus amyloliquefaciens* of which the amino-acid sequence has been altered, in particular with respect to use in washing and cleaning agents, in order to obtain improved cleaning performance, to the nucleic acids which code for said proteases, and to the preparation of said proteases. The present disclosure further relates to uses of said proteases, to methods in which said proteases are used, and to agents, in particular washing and cleaning agents, which contain said proteases.

BACKGROUND

Proteases are among the industrially most significant enzymes of all. In the context of washing and cleaning agents, proteases are the longest established enzymes that are contained in virtually all modern, high-performance washing and cleaning agents. They cause the breakdown of protein-containing stains on the item to be cleaned. Of these proteases, subtilisin-type proteases (subtilases, subtilopeptidases, EC 3.4.21.62) are particularly significant, which proteases are serine proteases owing to the catalytically active amino acids. Said proteases act as non-specific endopeptidases and hydrolyze any acid amide bonds that are within peptides or proteins. Their pH optimum is usually in the highly alkaline range. An overview of this family is found, for example, in the article "Subtilases: Subtilisin-like Proteases" by R. Siezen, pages 75-95 in "Subtilisin enzymes", published by R. Bott and C. Betzel, New York, 1996. Subtilases are formed naturally by microorganisms. Of these, subtilisins that are formed by and secreted from *Bacillus* species should be mentioned in particular as the most significant group within the subtilases.

Examples of the subtilisin-type proteases that are preferably used in washing and cleaning agents are the subtilisins BPN' and Carlsberg, protease PB92, subtilisins 147 and 309, protease from *Bacillus lentus*, in particular from *Bacillus lentus* DSM 5483, subtilisin DY, the enzymes thermitase, proteinase K and proteases TW3 and TW7, which belong to the subtilases but no longer to the subtilisins in the narrower sense, and variants of the mentioned proteases which have an altered amino-acid sequence by comparison with the starting protease. Proteases are altered, selectively or randomly, by methods known from the prior art, and are thereby optimized for use in washing and cleaning agents, for example. These methods include point, deletion or insertion mutagenesis, or fusion with other proteins or protein parts. Therefore, variants that are appropriately optimized are known for most of the proteases known from the prior art.

BRIEF SUMMARY

This disclosure provides a protease having an amino-acid sequence which is at least about 70% identical to the amino-acid sequence shown in SEQ ID NO:1 over the entire length thereof, and has the amino-acid substitutions S24G, S33T, S53G, S78N, S101N, G128A and L217Q, based in each case on the numbering according to SEQ ID NO:1.

This disclosure also provides a protease obtained from the aforementioned protease acting as a starting molecule by one or more conservative amino-acid substitutions, the protease having the amino-acid substitutions S24G, S33T, S53G, S78N, S101N, G128A and L217Q at the positions which correspond to positions 24, 33, 53, 78, 101, 128 and 217 according to SEQ ID NO:1; and/or acting as a starting molecule by fragmentation, deletion, insertion or substitution mutagenesis, and has an amino-acid sequence which matches that of the starting molecule over a length of at least about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 265, about 270 or about 275 interconnected amino acids, the protease having the amino-acid substitutions S24G, S33T, S53G, S78N, S101N, G128A and L217Q at the positions which correspond to positions 24, 33, 53, 78, 101, 128 and 217 according to SEQ ID NO:1.

This disclosure further provides a method for preparing a protease, including the step of substituting the amino acids at the positions which correspond to positions 24, 33, 53, 78, 101, 128 and 217 in SEQ ID NO:1 in a starting protease of which the sequence is at least about 70% identical to the amino-acid sequence shown in SEQ ID NO:1 over the entire length thereof, such that the protease has the amino acids 24G, 33T, 53G, 78N, 101N, 128A and 217Q at the corresponding positions.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Particularly preferred subtilisins which are commercially used in washing agents are the two proteases subtilisin Carlsberg and a variant of the *Bacillus lentus* DSM 5483 alkaline protease (BLAP) which, proceeding from wild-type BLAP, has the mutations S3T, V4I, V193M, V199I and L211D in the numbering according to BLAP (reference protease 1). It has surprisingly now been found that a subtilisin-type protease from *Bacillus amyloliquefaciens* or a reasonably similar protease (in terms of sequence identity) which has the amino-acid substitutions at positions S24G, S33T, S53G, S78N, S101N, G128A and L217Q, in each case based on the numbering according to SEQ ID NO:1, has improved cleaning performance with regard to various protein-containing stains by comparison with proteases from the prior art, in particular reference protease 1 and 2 (wild-type BLAP with the mutations S3T, V4I, V193M, V199I and L211D in the numbering according to BLAP and subtilisin Carlsberg), and is therefore particularly suitable for use in washing or cleaning agents.

Therefore, in a first aspect, the present disclosure relates to a protease which has an amino-acid sequence which is at least about 70% identical to the amino-acid sequence shown in SEQ ID NO:1 over the entire length thereof, and has the amino-acid substitutions S24G, S33T, S53G, S78N, S101N, G128A and L217Q, based in each case on the numbering according to SEQ ID NO:1.

The present disclosure further relates to a method for preparing a protease, comprising substituting the amino acids at the positions which correspond to positions 24, 33, 53, 78, 101, 128 and 217 in SEQ ID NO:1 in a starting protease of which the sequence is at least about 70% identical to the amino-acid sequence shown in SEQ ID NO:1 over the entire length thereof, such that the protease has the amino acids 24G, 33T, 53G, 78N, 101N, 128A and 217Q at the corresponding positions.

A "protease" within the meaning of the present patent application therefore covers both the protease as such and a protease prepared using a method as contemplated herein. All comments made with regard to the protease therefore relate to both the protease as a substance and the corresponding methods, in particular methods for preparing the protease.

Other aspects of the present disclosure relate to the nucleic acids which code for these proteases, to non-human host cells which contain proteases or nucleic acids as contemplated herein, to agents, in particular washing and cleaning agents, which comprise proteases as contemplated herein, to washing and cleaning methods, and to uses of the proteases as contemplated herein in washing or cleaning agents for removing protein-containing or peptide-containing stains.

"At least one", as used herein, means one or more, i.e. one, two, three, four, five, six, seven, eight, nine, ten, eleven, twelve, thirteen, fourteen, or more.

The present disclosure is based on the surprising finding that an alteration, as contemplated herein, of the positions which correspond to positions 4, 33, 53, 78, 101, 128 and 217 of a protease from *Bacillus amyloliquefaciens* according to SEQ ID NO:1 in a protease which has an amino-acid sequence that is at least about 70% identical to the amino-acid sequence shown in SEQ ID NO:1 such that the amino acids 24G, 33T, 53G, 78N, 101N, 128A and 217Q are present at the corresponding positions has improved cleaning performance with regard to various protein-containing stains by comparison with reference proteases 1 and 2. This is particularly surprising since reference proteases 1 and 2 are used commercially in washing agents and have been optimized for this purpose.

The proteases as contemplated herein are particularly stable in washing or cleaning agents, for example with respect to surfactants and/or bleaching agents and/or with respect to temperature effects, in particular with respect to high temperatures of, for example, between from about 30 and about 55° C., in particular about 40° C., and/or with respect to acidic or alkaline conditions and/or with respect to changes in pH and/or with respect to denaturing or oxidizing agents and/or with respect to proteolytic breakdown and/or with respect to a change in redox behaviors. Proteases of this kind that are improved in terms of performance provide for improved washing results on protease-sensitive stains in a wide temperature range.

A protease as contemplated herein has proteolytic activity, i.e. it is capable of hydrolyzing peptide bonds of a polypeptide or protein, in particular in a washing or cleaning agent. A protease as contemplated herein is therefore an enzyme which catalyzes the hydrolysis of peptide bonds and is therefore capable of cleaving peptides or proteins. Furthermore, a protease as contemplated herein is preferably a mature protease, i.e. the catalytically active molecule without signal peptide(s) and/or propeptide(s). Unless indicated otherwise, the specified sequences also each relate to mature enzymes.

In a further embodiment of the present disclosure, the protease has an amino-acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5% and about 98.8% identical to the amino-acid sequence shown in SEQ ID NO:1 over the entire length thereof, and has the amino acids 24G, 33T, 53G, 78N, 101N, 128A and 217Q at the positions which correspond to positions 24, 33, 53, 78, 101, 128 and 217 in the numbering according to SEQ ID NO:1. In the context of the present disclosure, the feature whereby a protease has the stated substitutions means that it contains all corresponding amino acids at the corresponding positions, i.e. none of the seven positions are otherwise mutated or deleted, for example by fragmentation of the protease. A protease of this kind that is preferred as contemplated herein is shown in SEQ ID NO:2.

The identity of nucleic-acid or amino-acid sequences is determined by a sequence comparison. This sequence comparison is based on the BLAST algorithm (cf. for example Altschul, S. F., Gish, W., Miller, W., Myers, E. W. & Lipman, D. J. (1990) "Basic local alignment search tool." J. Mol. Biol. 215:403-410 and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pages 3389-3402) which is established and commonly used in the prior art and is carried out, in principle, by similar series of nucleotides or amino acids in the nucleic-acid or amino-acid sequences being assigned to one another. The assignment of the relevant positions shown in a table is referred to as an "alignment". Another algorithm available from the prior art is the FASTA algorithm. Sequence comparisons (alignments), in particular multiple sequence comparisons, are generated using computer programs. For example, the Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on these programs or algorithms are often used. In the present patent application, all sequence comparisons (alignments) are generated using the computer program Vector NTI® Suite 10.3 (Invitrogen Corporation, 1600 Faraday Avenue, Carlsbad, Calif., USA) with the specified standard parameters, the AlignX-Modul of which program for the sequence comparisons is based on ClustalW.

A comparison of this kind makes it possible to specify the similarity between the compared sequences. This similarity is usually expressed in percent identity, i.e. the percentage of identical nucleotides or amino-acid residues at the same positions or at positions that correspond to one another in an alignment. In amino-acid sequences, the broader concept of "homology" factors in conserved amino-acid exchanges, i.e. amino acids having similar chemical activity, since these usually have similar chemical activities within the protein. Therefore, the similarity between the compared sequences can also be expressed in percent homology or percent similarity. Information relating to identity and/or homology may apply to the entirety of the polypeptides or genes or only to individual segments. Homologous or identical segments of different nucleic-acid or amino-acid sequences are therefore defined by matches in the sequences. Segments of this kind often have identical functions. Said segments may be small and only comprise a few nucleotides or amino acids. Segments that are this small often perform functions that are essential to the overall activity of the protein. Therefore, it may be expedient for sequence matches to only relate to individual, optionally small, segments. However, unless indicated otherwise, information relating to identity or homology in the present application relates to the entire length of the nucleic-acid or amino-acid sequence specified in each case.

In the context of the present disclosure, if it is stated that an amino-acid position corresponds to a numerically identified position in SEQ ID NO:1, this means that the corresponding position is assigned to the numerically identified position in SEQ ID NO:1 in an alignment as defined above.

In a further embodiment of the present disclosure, the protease cleaning performance is not significantly reduced by comparison with that of a protease which has an amino-acid sequence that corresponds to the amino-acid sequence shown in SEQ ID NO:1 or in SEQ ID NO:2, i.e. said protease has at least about 80%, preferably at least about 100%, more preferably at least about 110%, of the reference washing performance. The cleaning performance can be determined in a washing system which contains a washing agent in a dosage of between from about 4.5 and about 7.0 grams per liter of washing liquor, and the protease, the proteases to be compared being used in the same concentration (based on the active protein) and the cleaning performance with respect to a stain on cotton is determined by measuring the extent to which the washed textiles have been cleaned. For example, the washing process can be carried out for about 60 minutes at a temperature of about 40° C., and the water can have a water hardness of between from about 15.5 and about 16.5° (German degree of hardness). The concentration of the protease in the washing agent intended for this washing system is from about 0.0001 to about 1.0 wt. %, preferably from about 0.006 to about 0.6 wt. %, based on the purified active protein.

A liquid reference washing agent for a washing system of this kind can be composed as follows (all amounts are given in percent by weight): about 7% of alkyl benzene sulfonic acid, about 9% of further anionic surfactants, about 4% of C12-C18 Na salts of fatty acids (soaps), about 7% of non-ionic surfactants, about 0.7% of phosphonates, about 3.2% of citric acid, about 3.0% of NaOH, about 0.04% of defoamers, about 5.7% of 1,2-propanediol, about 0.1% of preservatives, about 2% of ethanol, about 0.2% of dye-transfer-inhibitors, and the remaining percentage of demineralized water. The dosage of the liquid washing agent is preferably between from about 4.5 and about 6.0 grams per liter of washing liquor, for example about 4.7, about 4.9 or about 5.9 grams per liter of washing liquor. Washing is preferably carried out within a pH range of between from about pH 8 and about pH 10.5, preferably between from about pH 8 and about pH 9.

Within the scope of the present disclosure, the cleaning performance is determined at about 40° C. using a liquid washing agent as specified above, the washing process preferably being carried out for about 60 minutes.

The degree of whiteness, i.e. the lightening of the stains, is preferably determined using optical measurement methods, preferably photometrically, as a measure of cleaning performance. A device suitable for this purpose is the spectrometer Minolta CM508d, for example. The devices used for the measurement are usually calibrated, in advance, against a white standard, preferably a white standard that is supplied therewith.

Each protease being applied in an identical manner in terms of activity ensures that the relevant enzymatic properties, i.e. for example cleaning performance on particular stains, are compared even if there is some kind of divergence in the ratio of active substance to overall protein (the values for specific activity). In general, low specific activity can be compensated for by adding a larger amount of protein.

A person skilled in the art of enzyme technology is familiar with methods for determining protease activity, and he uses said methods as a matter of routine. For example, methods of this kind are disclosed in Tenside, Band 7 (1970), pages 125-132. Alternatively, protease activity can be determined by releasing the chromophore para-nitroaniline (pNA) from the substrate suc-L-Ala-L-Ala-L-Pro-L-Phe-p-nitroanilide (AAPF). The protease cleaves the substrate and releases pNA. The release of pNA causes an increase in the extinction at about 410 nm, the temporal progression of which is a measure of enzymatic activity (cf. Del Mar et al., 1979). The measurement is taken at a temperature of about 25° C., a pH of about 8.6, and a wavelength of about 410 nm. The measurement time is about 5 min and the measurement interval is from about 20 s to about 60 s. Protease activity is usually expressed in protease units (PU). Suitable protease activities are, for example, about 2.25, about 5 or about 10 PU per ml of washing liquor. However, the protease activity is not zero.

An alternative test for establishing the proteolytic activity of the proteases as contemplated herein is an optical measurement method, preferably a photometric method. The test suitable for this purpose comprises the protease-dependent cleavage of the substrate protein casein. Said protein is cleaved by the protease into a plurality of smaller subproducts. All of these subproducts have an increased absorption at about 290 nm by comparison with uncleaved casein, this increased absorption being determined using a photometer, and it thus being possible to draw a conclusion on the enzymatic activity of the protease.

The protein concentration can be determined using known methods, for example the BCA method (bicinchoninic acid; 2,2'-biquinolyl-4,4'-dicarboxylic acid) or the Biuret method (A. G. Gornall, C. S. Bardawill and M. M. David, J. Biol. Chem., 177 (1948), pages 751-766). The active protein concentration can be determined, in this respect, by titrating the active centers using a suitable irreversible inhibitor (for proteases, phenylmethylsulfonyl fluoride (PMSF), for example), and determining the residual activity (cf. M. Bender et al., J. Am. Chem. Soc. 88, 24 (1966), pages 5890-5913).

In addition to the aforementioned amino-acid alterations, proteases as contemplated herein can have further amino-acid alterations, in particular amino-acid substitutions, insertions or deletions. Proteases of this kind are developed, for example, by targeted genetic alteration, i.e. by mutagenesis methods, and optimized for particular uses or in respect of specific properties (for example in respect of their catalytic activity, stability, etc.). Furthermore, nucleic acids as contemplated herein can be incorporated in recombination approaches and are thus used to produce completely new types of proteases or other polypeptides.

The aim is to introduce targeted mutations, such as substitutions, insertions or deletions, into known molecules, in order to improve the cleaning performance of enzymes as contemplated herein, for example. For this purpose, in particular the surface charges and/or isoelectric point of the molecules, and thus their interactions with the substrate, can be altered. For example, the net charge of the enzymes can be changed in order to thereby influence the substrate binding, in particular for use in washing and cleaning agents. Alternatively or in addition, the stability of the protease can be increased further still, and thus the cleaning performance thereof can be improved, by one or more appropriate mutations. Advantageous properties of individual mutations, e.g. individual substitutions, may complement one another. A protease that has already been optimized in terms of particular properties, for example in terms of the stability thereof with respect to surfactants and/or bleaching agents and/or other components, can therefore also be developed within the scope of the present disclosure.

In order to describe substitutions that affect exactly one amino-acid position (amino-acid exchanges), the following convention is used: the internationally conventional single-letter code of the naturally present amino acid is given first, and then the associated sequence position, and finally the amino acid that has been added. Several exchanges within the same polypeptide chain are separated from one another by slashes. For insertions, additional amino acids are indicated after the sequence position. For deletions, the amino acid that has been removed is replaced with a symbol, for example a star or a dash, or a Δ is put before the corresponding position. For example, S24G denotes the substitution of serine at position 24 by glycine, S24AG denotes the insertion of glycine after the amino acid alanine at position 24, and S24* or ΔS24 denotes the deletion of serine from position 24. This nomenclature is known to a person skilled in the art of enzyme technology.

Therefore, the present disclosure further relates to a protease which can be obtained from a protease as described above acting as a starting molecule by employing one or more conservative amino-acid substitutions, the protease still having in the numbering according to SEQ ID NO:1 the amino-acid substitutions as contemplated herein at the positions which correspond to positions 24, 33, 53, 78, 101, 128 and 217 in SEQ ID NO:1, as described above. The term "conservative amino-acid substitutions" means the exchange (substitution) of an amino-acid residue with another amino-acid residue, this exchange not resulting in a change in the polarity or charge at the position of the exchanged amino acid, e.g. the exchange of a nonpolar amino-acid residue with another nonpolar amino-acid residue. Within the scope of the present disclosure, conservative amino-acid substitutions include for example: G=A=S, I=V=L=M, D=E, N=Q, K=R, Y=F, S=T, G=A=I=V=L=M=Y=F=W=P=S=T.

Alternatively or in addition, the protease can be obtained from a protease as contemplated herein acting as a starting molecule by employing fragmentation, deletion, insertion or substitution mutagenesis and has an amino-acid sequence which matches that of the starting molecule over a length of at least about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 265, about 270 or about 275 interconnected amino acids, the mutated amino-acid residues contained in the starting molecule still being present at the positions which correspond to positions 24, 33, 53, 78, 101, 128 and 217 in SEQ ID NO:1.

It is thus possible, for example, for individual amino acids to be deleted from the enzyme termini or loops, without this resulting in the proteolytic activity being lost or reduced. Furthermore, by employing fragmentation, deletion, insertion or substitution mutagenesis of this kind, the allergenicity of relevant enzymes, for example, can also be reduced and thus the usability thereof can be improved overall. The enzymes advantageously still have their proteolytic activity even after the mutagenesis, i.e. the proteolytic activity thereof corresponds at least to that of the starting enzyme, i.e. in a preferred embodiment, the proteolytic activity is at least about 80%, preferably at least about 90%, of the activity of the starting enzyme. Other substitutions can also have advantageous effects. It is possible to exchange a single amino acid or several interconnected amino acids with other amino acids.

In this case, the other amino-acid positions are defined by an alignment of the amino-acid sequence of a protease as contemplated herein with the amino-acid sequence of the protease from *Bacillus amyloliquefaciens*, as shown in SEQ ID NO:1. Furthermore, the assignment of the positions is determined by the mature protein. In particular, this assignment is also used if the amino-acid sequence of a protease as contemplated herein has a higher number of amino-acid residues than the protease from *Bacillus amyloliquefaciens* according to SEQ ID NO:1. Proceeding from the mentioned positions in the amino-acid sequence of the protease from *Bacillus amyloliquefaciens*, the alteration positions in a protease as contemplated herein are those which are precisely assigned to these positions in an alignment.

Advantageous positions for sequence alterations, in particular substitutions, of the protease from *Bacillus amyloliquefaciens* which when transferred to homologous positions of the proteases as contemplated herein are preferably of significance and impart advantageous functional properties to the protease are therefore positions 24, 33, 53, 78, 101, 128 and 217, for assignment in an alignment with SEQ ID NO:1 and thus in the numbering according to SEQ ID NO:1. At the stated positions, the following amino-acid residues are present in the reference protease from *Bacillus amyloliquefaciens*: S24, S33, S53, S78, S101, G128 and L217.

Further confirmation of the correct assignment of the amino acids to be altered, i.e. in particular of the functional correspondence thereof, can be provided by comparison tests during which the two positions assigned to one another on the basis of an alignment are altered in the same way in the two proteases being compared with one another and it is observed whether the enzymatic activity is altered in the same way in the two proteases. If, for example, an amino-acid exchange at a particular position of the protease from *Bacillus amyloliquefaciens* according to SEQ ID NO:1 is associated with a change in an enzymatic parameter, for example with the increase in the $K_M$ value, and if a corresponding change in the enzymatic parameter, thus for example also an increase in the $K_M$ value, is observed in a protease variant as contemplated herein of which the amino-acid exchange was achieved by the same added amino acid, this is considered to be confirmation of the correct assignment.

All elements specified can also be applied to the methods as contemplated herein for preparing a protease. A method as contemplated herein therefore further comprises one or more of the following method steps:

a) introducing one or more conservative amino-acid substitutions, the protease in the numbering according to SEQ ID NO:1 having the amino-acid substitutions 24G, 33T, 53G, 78N, 101N, 128A and 217Q; b) altering the amino-acid sequence by employing fragmentation, deletion, insertion or substitution mutagenesis such that the protease has an amino-acid sequence which matches that of the starting molecule over a length of at least about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 265, about 270 or about 275 interconnected amino acids, the amino-acid substitutions 24G, 33T, 53G, 78N, 101N, 128A and 217Q contained in the starting molecule still being present.

All comments made also apply to the methods as contemplated herein.

In further embodiments of the present disclosure, the protease or the protease prepared using a method as contemplated herein is still at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5% or about 98.8% identical to the amino-acid sequence shown in SEQ ID NO:2 over the entire length thereof. Alternatively, the protease or the protease prepared using a method as contemplated herein is still at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5% or about 98% identical to the amino-acid sequence shown in SEQ ID NO:1 over the entire length thereof. The protease or the protease prepared using a method as contemplated herein has the amino-acid substitutions 24G, 33T, 53G, 78N, 101N, 128A and 217Q.

The present disclosure also relates to a protease as described above which is additionally stabilized, in particular by employing one or more mutations, for example substitutions, or by being coupled to a polymer. Increasing stability during storage and/or during use, for example during the washing process, leads to the enzymatic activity being maintained for longer and thus to the cleaning performance being improved. In principle, all stabilizing possibilities that are expedient and/or described in the prior art can be considered for this. Stabilizations which are achieved by employing mutations of the enzyme itself are preferred, since stabilizations of this kind do not require any further working steps after the enzyme has been obtained. Examples of sequence alterations suitable for this purpose have been mentioned above. Further suitable sequence alterations are known from the prior art. For example, proteases can also be stabilized by one or more tyrosine residues being exchanged with other amino acids.

Further possibilities for stabilization include for example: altering the binding of metal ions, in particular the calcium binding sites, for example by exchanging one or more of the amino acid(s) that are involved in the calcium binding with one or more negatively charged amino acids and/or by introducing sequence alterations in at least one of the sequences of the two amino acids arginine and glycine;

protecting against the influence of denaturing agents, such as surfactants, by utilizing mutations which cause the amino-acid sequence to be altered on or at the surface of the protein;

exchanging amino acids which are close to the N-terminus with amino acids which are assumed to come into contact with the rest of the molecule by utilizing non-covalent interactions, and thus contribute to maintaining the globular structure.

Preferred embodiments are those in which the enzyme is stabilized in several different ways, since several stabilizing mutations have a cumulative or synergistic effect.

The present disclosure also relates to a protease as described above which has at least one chemical modification. A protease that is altered in this way is referred to as a "derivative", i.e. the protease is derivatized.

Within the meaning of the present application, "derivatives" are therefore understood to mean proteins of which the pure amino-acid chain has been modified chemically. Derivatizations of this kind can be carried out in vivo, for example, by the host cell which expresses the protein. In this respect, couplings to low-molecular-weight compounds, such as lipids or oligosaccharides, are of particular importance. However, derivatizations may also be carried out in vitro, for example by the chemical conversion of a side chain of an amino acid or by covalent bonding of another compound to the protein. For example, it is possible to couple amines to carboxyl groups of an enzyme in order to change the isoelectric point. This other compound may also be another protein which is bound to a protein as contemplated herein via bifunctional chemical compounds, for example. Derivatization is also understood to mean covalent bonding to a macromolecular carrier, or non-covalent inclusion in suitable macromolecular cage structures. Derivatizations can, for example, influence the substrate specificity or the bond strength to the substrate or cause temporary inhibition of enzymatic activity, if the coupled substance is an inhibitor. This can be expedient in terms of the period of storage, for example. Modifications of this kind can also influence stability or enzymatic activity. They can also be used to reduce the allergenicity and/or immunogenicity of the protein and to thus increase the skin compatibility thereof, for example. For example, couplings to macromolecular compounds, for example polyethylene glycol, can improve the protein in terms of stability and/or skin compatibility.

In the broadest sense, derivatives of a protein as contemplated herein can be understood to also include preparations of these proteins. Depending on how a protein is obtained, recovered or prepared, said protein can be accompanied by a wide range of other substances, for example from the culture of the microorganisms that produce it. A protein may also have been deliberately mixed with other substances in order to increase its storage stability, for example. Therefore, the present disclosure also covers all preparations of a protein as contemplated herein. This is still true irrespective of whether or not this enzymatic activity actually develops in a particular preparation. This is because it may be desirable for the protein to not have any activity or to only have low activity when being stored, and for the enzymatic function to only develop once the protein is in use. This can be controlled, for example, by appropriate accompanying substances. In particular, in this respect, it is possible to jointly prepare proteases and protease inhibitors.

With regard to all above-described proteases or protease variants and/or derivatives, within the scope of the present disclosure, proteases, protease variants and/or derivatives of which the stability and/or activity corresponds at least to that of the protease according to SEQ ID NO:2 and/or of which the cleaning performance corresponds at least to that of the protease according to SEQ ID NO:2 are particularly preferred, the cleaning performance being determined in a washing system, as described above.

The present disclosure also relates to a nucleic acid which codes for a protease as contemplated herein, and to a vector containing a nucleic acid of this kind, in particular a cloning vector or an expression vector.

These may be DNA or RNA molecules. They may be present as a single strand, as a single strand that is complementary to the first single strand, or as a double strand. In the case of DNA molecules in particular, the sequences of the two complementary strands should be taken into account in all three possible reading frames. It should also be noted that different codons, i.e. base triplets, can code for the same amino acids, such that a particular amino-acid sequence can be coded for by several different nucleic acids. Owing to this degeneracy of the genetic code, all nucleic-acid sequences which can code for one of the above-described proteases are included in this subject of the present disclosure. A person skilled in the art is able to identify these nucleic-acid sequences with absolute certainty since, despite the degeneracy of the genetic code, defined amino acids can be assigned to individual codons. Therefore, proceeding from an amino-acid sequence, a person skilled in the art can easily identify nucleic acids which code for said amino-acid sequence. Furthermore, in nucleic acids as contemplated herein, one or more codons can be replaced by synonymous codons. This aspect relates in particular to the heterologous expression of the enzymes as contemplated herein. Therefore, each organism, for example a host cell of a production strain, has a particular codon usage. "Codon usage" is understood to mean the translation of the genetic code into amino acids by utilizing the relevant organism. Bottlenecks can occur in protein biosynthesis if the codons on the nucleic acid are accompanied by a comparatively low number of charged tRNA molecules in the organism. Although coding for the same amino acid, this leads to a codon being translated less efficiently in the organism than a synonymous codon which codes for the same amino acid. Owing to the presence of a higher number of tRNA molecules for the synonymous codon, said codon can be translated more efficiently in the organism.

Using methods which are currently generally known, such as chemical synthesis or polymerase chain reaction (PCR), in conjunction with standard methods in molecular biology and/or protein chemistry, it is possible for a person skilled in the art, on the basis of known DNA and/or amino-acid sequences, to produce the corresponding nucleic acids and even complete genes. Methods of this kind are known from, for example, Sambrook, J., Fritsch, E. F. and Maniatis, T. 2001. Molecular cloning: a laboratory manual, 3rd Edition Cold Spring Laboratory Press.

Within the meaning of the present disclosure, vectors are understood to mean elements which include nucleic acids and which contain a nucleic acid as contemplated herein as a nucleic-acid range. Vectors allow establishment of this nucleic acid in a species or a cell line over multiple generations or cell divisions as a stable genetic element. Vectors are specific plasmids, i.e. circular genetic elements, in particular for use in bacteria. Within the scope of the present disclosure, a nucleic acid as contemplated herein is cloned in a vector. These may include vectors, for example, which originate from bacterial plasmids, from viruses, or from bacteriophages, or predominantly synthetic vectors or plasmids having elements of various origins. Using the further genetic elements which are present in each case, vectors are able to become established as stable units in the host cells in question over several generations. They may be present as separate units outside of a chromosome or be integrated in a chromosome or chromosomal DNA.

Expression vectors have nucleic-acid sequences which enable them to replicate in the host cells, preferably microorganisms, particularly preferably bacteria, which contain them and to express therein a contained nucleic acid. The expression is influenced, in particular, by promoter(s) which regulate the transcription. In principle, the expression can be carried out by the natural promoter which is originally located in front of the nucleic acid to be expressed, by a promoter of the host cell provided on the expression vector, or by a modified or completely different promoter of another organism or another host cell. In the present case, at least one promoter is provided for the expression of a nucleic acid as contemplated herein and is used for the expression thereof. Expression vectors can also be regulated, for example by changing the culturing conditions, by reaching a particular cell density in the host cells containing said vectors, or by adding particular substances, in particular activators for gene expression. An example of a substance of this kind is the galactose derivative isopropyl-β-D-thiogalactopyranoside (IPTG) which is used as an activator for the bacterial lactose operon (lac operon). Unlike in expression vectors, the contained nucleic acid in cloning vectors is not expressed.

The present disclosure also relates to a non-human host cell containing a nucleic acid as contemplated herein or a vector as contemplated herein, or containing a protease as contemplated herein, in particular a non-human host cell which secretes the protease into the medium surrounding the host cell. A nucleic acid as contemplated herein or a vector as contemplated herein is preferably transformed into a microorganism which then constitutes a host cell as contemplated herein. Alternatively, individual components, i.e. nucleic-acid parts or fragments of a nucleic acid as contemplated herein, can be introduced into a host cell such that the resulting host cell contains a nucleic acid as contemplated herein or a vector as contemplated herein. This procedure is particularly suitable if the host cell already contains one or more components of a nucleic acid as contemplated herein or of a vector as contemplated herein, and the additional components are then added accordingly. Methods for transforming cells are established in the prior art and are sufficiently known to a person skilled in the art. In principle, all cells, i.e. prokaryotic or eukaryotic cells, are suitable as host cells. Preferred host cells are those which may be advantageously managed genetically, which involves, for example, transformation using the nucleic acid or the vector and stable establishment thereof, for example unicellular fungi or bacteria. In addition, preferred host cells are distinguished by good microbiological and biotechnological manageability. This relates, for example, to ease of culturing, high growth rates, low demands on fermentation media, and good production and secretion rates for foreign proteins. Preferred host cells as contemplated herein secrete the (transgenically) expressed protein into the medium surrounding the host cells. Furthermore, the proteases can be modified, following preparation, by the cells that produced them, for example by the attachment of sugar molecules, by formylations, by aminations, etc. Post-translational modifications of this kind can influence the protease in terms of its function.

Those host cells of which the activity can be regulated due to genetic regulation elements which are provided on the vector, for example, but which may also be present in these cells from the outset, represent other preferred embodiments. These host cells may be induced to express, for example by the controlled addition of chemical compounds which are used as activators, by changing the culturing conditions, or upon reaching a particular cell density. This provides for cost-effective production of the proteins as contemplated herein. An example of a compound of this kind is IPTG, as described above.

Prokaryotic or bacterial cells are preferred host cells. Bacteria are distinguished by short generation times and low demands on the culturing conditions. Cost-effective culturing methods or preparation methods can thereby be established. Furthermore, a person skilled in the art has a vast pool of experience with regard to bacteria in fermentation technology. Gram-negative or gram-positive bacteria may be suitable for specific production for a wide variety of reasons, which should be determined by experiment in any given case, for example nutrient sources, product formation rate, time constraints, etc.

In the case of gram-negative bacteria, such as *Escherichia coli*, numerous proteins are secreted into the periplasmatic space, i.e. the compartment between the two membranes which enclose the cells. This may be advantageous for specific applications. Furthermore, gram-negative bacteria may also be formed such that they secrete the expressed proteins not only into the periplasmatic space, but also into the medium surrounding the bacterium. By contrast, gram-positive bacteria, for example *Bacilli* or actinomycetes or other representatives of the actinomycetales, have no outer membrane, and therefore secreted proteins are released directly into the medium surrounding the bacteria, generally the nutrient medium, from which the expressed proteins may be purified. They may be isolated directly from the medium or processed further. Moreover, gram-positive bacteria are related to or identical to most origin organisms for industrially significant enzymes and they themselves usually form comparable enzymes, such that they have a similar codon usage and the protein synthesis apparatus thereof is naturally aligned accordingly.

Host cells as contemplated herein may be altered in terms of their requirements for culture conditions, may have different or additional selection markers, or may express different or additional proteins. These host cells may be in particular host cells that express a plurality of proteins or enzymes transgenically.

The present disclosure can be used, in principle, for all microorganisms, in particular for all fermentable microorganisms, particularly preferably for those from the Bacillus genus, and leads to it being possible to prepare proteins as contemplated herein by using microorganisms of this kind. Microorganisms of this kind then constitute host cells within the meaning of the present disclosure.

In a further embodiment of the present disclosure, the host cell is a bacterium, preferably a bacterium selected from the group of the genera of *Escherichia, Klebsiella, Bacillus, Staphylococcus, Corynebacterium, Arthrobacter, Streptomyces, Stenotrophomonas* and *Pseudomonas*, more preferably a bacterium selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor* and *Stenotrophomonas maltophilia*.

However, the host cell may also be a eukaryotic cell which has a nucleus. Therefore, the present disclosure further relates to a host cell which has a nucleus. Unlike prokaryotic cells, eukaryotic cells are able to modify the formed protein post-translationally. Examples of eukaryotic cells are fungi such as actinomycetes or yeasts such as *Saccharomyces* or *Kluyveromyces*. This may be particularly advantageous, for example, if, in the context of their synthesis, the proteins are intended to undergo specific modifications which systems of this kind allow. The modifications which are carried out by eukaryotic systems, particularly in the context of protein synthesis, include, for example, the binding of low-molecular-weight compounds such as membrane anchors or oligosaccharides. Oligosaccharide modifications of this kind may be desirable, for example, as a way to reduce the allergenicity of an expressed protein. A co-expression with the enzymes formed naturally by cells of this kind, such as cellulases or lipases, can also be advantageous. Furthermore, thermophilic fungal expression systems, for example, may be particularly suitable for expressing temperature-resistant proteins or variants.

The host cells as contemplated herein are cultured and fermented in a conventional manner, for example in batch or continuous systems. In the first case, a suitable nutrient medium is inoculated with the host cells, and the product is harvested from the medium after a period of time that can be determined by experiment. Continuous fermentation is distinguished by the achievement of a steady state in which, over a comparatively long period of time, some cells die, but also regenerate, and at the same time, the formed protein can be removed from the medium.

Host cells as contemplated herein are preferably used in order to prepare proteases as contemplated herein. Therefore, the present disclosure also relates to a method for preparing a protease, comprising:

a) culturing a host cell as contemplated herein, and
b) isolating the protease from the culture medium or from the host cell.

This subject of the present disclosure preferably includes fermentation methods. Fermentation methods are known per se from the prior art, and constitute the actual large-scale production step, generally followed by a suitable method for purifying the prepared product, for example the protease as contemplated herein. All fermentation methods which are based on a corresponding method for preparing a protease as contemplated herein constitute embodiments of this subject of the present disclosure.

Fermentation methods which are exemplified in that the fermentation is carried out via an inflow strategy are in particular considered. Here, the media components that are consumed by the continuous culturing are fed in. Significant increases both in the cell density and in the cell mass or dry mass, and/or in particular in the activity of the protease of interest, can be achieved in this way. Furthermore, the fermentation may also be designed in such a way that undesirable metabolic products are filtered out, or neutralized by adding a buffer or appropriate counterions.

The prepared protease can be harvested from the fermentation medium. A fermentation method of this kind is preferred over isolation of the protease from the host cell, i.e. product recovery from the cell mass (dry mass); however, said method requires that suitable host cells or one or more suitable secretion markers or mechanisms and/or transport systems be provided, so that the host cells secrete the protease into the fermentation medium. Alternatively, without secretion, the protease can be isolated from the host cell, i.e. separated from the cell mass, for example by precipitation with ammonium sulfate or ethanol, or by chromatographic purification.

All aforementioned elements can be combined to form methods for preparing proteases as contemplated herein.

The present disclosure also relates to an agent which contains a protease as contemplated herein, as described above. The agent is preferably a washing or cleaning agent.

This covers all conceivable types of washing or cleaning agents, including both concentrates and agents to be used in undiluted form, for use on a commercial scale in washing machines or for washing or cleaning by hand. These agents include, for example, washing agents for textiles, carpets or natural fibers for which the term "washing agent" is used. These also include, for example, dishwashing detergents for dishwashers or manual dishwashing detergents or cleaners for hard surfaces, such as metal, glass, porcelain, ceramics, tiles, stone, coated surfaces, plastics materials, wood or leather for which the term "cleaning agent" is used, i.e. in addition to manual and automatic dishwashing detergents, also abrasive cleaners, glass cleaners, WC rimblocks, etc. Within the scope of the present disclosure, the washing and cleaning agents also include auxiliary washing agents, which are added to the actual washing agent when washing textiles manually or using a machine in order to achieve an additional effect. Furthermore, within the scope of the present disclosure, washing and cleaning agents also include textile pre-treatment and post-treatment agents, i.e. agents with which the piece of laundry comes into contact before it is actually washed, for example in order to loosen stubborn dirt, and also agents which impart other desirable properties to the laundry, for example softness to touch, crease resistance or low static charge, in a step that comes after the actual textile washing process. The agents mentioned last include, inter alia, softeners.

The washing or cleaning agents as contemplated herein, which may be present in the form of powdered solids, compressed particles, homogeneous solutions or suspensions, can contain, in addition to a protease as contemplated herein, all known ingredients that are common in agents of this kind, at least one further ingredient preferably being present in the agent. The agents as contemplated herein may contain surfactants, builders, peroxygen compounds or bleach activators, in particular. They may also contain water-miscible organic solvents, further enzymes, sequestering agents, electrolytes, pH regulators and/or further auxiliaries such as optical brighteners, graying inhibitors, foam regulators, and dyes and fragrances, and combinations thereof.

In particular, a combination of a protease as contemplated herein with one or more further ingredient(s) of the agent is advantageous, since an agent of this kind has improved cleaning performance in preferred embodiments as contemplated herein on account of synergies obtained thereby. In particular, such synergy can be achieved by the combination of a protease as contemplated herein with a surfactant and/or a builder and/or a peroxygen compound and/or a bleach activator.

Advantageous ingredients of agents as contemplated herein are disclosed in international patent application WO2009/121725, starting on the penultimate paragraph of page 5 and ending on page 13 after the second paragraph. Reference is made explicitly to this disclosure and the content thereof is incorporated in the present patent application.

In various embodiments, the agent as contemplated herein contains anionic surfactants. Suitable anionic surfactants are in particular soaps and those containing sulfate or sulfonate groups preferably having alkali ions as cations. Soaps that can be used are preferably the alkali salts of saturated or unsaturated fatty acids having from about 12 to about 18 C atoms, in particular C12-C18 fatty acid sodium salts. These are preferably contained in the agent in an amount of between from about 1 wt. % and about 7 wt. %, particularly preferably between from about 3 wt. % and about 5 wt. %. Generally, fatty acids may also be used in a not completely neutralized form. Sulfate-type surfactants that can be used include the salts of sulfuric acid semiesters of fatty alcohols having from about 12 to about 18 C atoms and the sulfation products of the mentioned non-ionic surfactants having a low degree of ethoxylation. Sulfonate-type surfactants that can be used include linear alkylbenzene sulfonates having from about 9 to about 14 C atoms in the alkyl portion, alkanesulfonates having from about 12 to about 18 C atoms, and olefin sulfonates having from about 12 to about 18 C atoms, resulting from the reaction of corresponding monoolefins with sulfur trioxide, and alpha-sulfo fatty acid esters, resulting from the sulfonation of fatty acid methyl or ethyl esters. The sulfonate-type surfactants are preferably contained in the agent in an amount of between from about 4 wt. % and about 10 wt. %, particularly preferably between from about 6 wt. % and about 8 wt. %.

Furthermore, the agent may contain non-ionic surfactants. Non-ionic surfactants suitable for washing and cleaning agents are known from international patent application WO2009/121725. They are preferably contained in the agent as contemplated herein in an amount of between from about 6 wt. % and about 12 wt. %, particularly preferably between from about 8 wt. % and about 10 wt. %.

In addition, the agent described herein may contain at least one builder. Known builders are disclosed in WO2009/121725. In the agent as contemplated herein, the preferred builders are citric acid/citrate and/or phosphonate. Citrate/citric acid is preferably contained in the agent in an amount of between from about 0.5 wt. % and about 6 wt. %, particularly preferably between from about 2 wt. % and about 4 wt. %. The preferred phosphonate content in the agent as contemplated herein is between from about 0.4 wt. % and about 1.0 wt. %, and particularly preferably between from about 0.6 wt. % and about 0.8 wt. %.

In order to stabilize the enzyme, the agent may also contain known stabilizers. In this context, 1,2-propanediol is preferably used. 1,2-propanediol can be contained in the agent as contemplated herein in an amount of between from about 3 wt. % and about 9 wt. %, preferably between from about 5 wt. % and about 7 wt. %.

An agent as contemplated herein preferably contains the protease in an amount of from about 2 μg to about 20 mg, preferably from about 5 μg to about 17.5 mg, particularly preferably from about 20 μg to about 15 mg, and very particularly preferably from about 50 μg to about 10 mg per g of the agent. Furthermore, the protease contained in the agent and/or further ingredients of the agent may be encapsulated in a substance that is impermeable to the enzyme at room temperature or in the absence of water, which substance becomes permeable to the enzyme under use conditions of the agent. Such an embodiment of the present disclosure is thus exemplified in that the protease is encapsulated in a substance that is impermeable to the protease at room temperature or in the absence of water. Furthermore, the washing or cleaning agent itself can also be packaged in a container, preferably an airtight container, from which it is released shortly before use or during the washing process.

In other embodiments of the present disclosure, the agent
a) is present in solid form, in particular as a flowable powder having a bulk density of from about 300 g/l to about 1200 g/l, in particular from about 500 g/l to about 900 g/l, or b) is present in paste or liquid form, and/or
c) is present in gel or pouch form, and/or
d) is present as a single-component system, or
e) is divided into a plurality of components.

These embodiments of the present disclosure cover all solid, powder, liquid, gel or paste dosage forms of agents as contemplated herein that may optionally also include a plurality of phases, and may be present in compressed or uncompressed form. The agent may be present in the form of a flowable powder, in particular having a bulk density of from about 300 g/l to about 1200 g/l, more particularly from about 500 g/l to about 900 g/l or from about 600 g/l to about 850 g/l. The solid dosage forms of the agent also include extrudates, granules, tablets or pouches. Alternatively, the agent may also be a liquid, gel or paste, for example in the form of a non-aqueous liquid washing agent or a non-aqueous paste or in the form of an aqueous liquid washing agent or water-containing paste. Furthermore, the agent may be present as a single-component system. Agents of this kind include one phase. Alternatively, an agent can also include a plurality of phases. An agent of this kind is therefore divided into a plurality of components.

Washing agents, in particular liquid washing agents, are particularly preferred as contemplated herein. Liquid washing agents of this kind can comprise, in addition to the protease, anionic surfactants, in particular linear alkylbenzene sulfonates, non-ionic surfactants, and at least one builder. In one embodiment of the present disclosure, a liquid washing agent of this kind comprises, in each case based on the total weight of the agent:
a) from about 4 wt. % to about 10 wt. %, preferably from about 6 wt. % to about 8 wt. %, of a linear alkylbenzene sulfonate;
b) from about 6 wt. % to about 12 wt. %, preferably from about 8 wt. % to about 10 wt. %, of a further anionic surfactant, in particular an alkyl ether sulfate;
c) from about 0.5 wt. % to about 6 wt. %, preferably from about 2 wt. % to about 4 wt. %, of citrate;
d) from about 0.4 to about 1.0 wt. %, preferably from about 0.6 to about 0.8 wt. %, of at least one phosphonate; and
e) optionally from about 3 wt. % to about 9 wt. %, preferably from about 5 wt. % to about 7 wt. %, of 1,2-propanediol.

Washing or cleaning agents as contemplated herein may only contain a protease. Alternatively, they may also contain further hydrolytic enzymes or other enzymes in a concentration that is expedient in terms of the effectiveness of the agent. Another embodiment of the present disclosure thus relates to agents which also comprise one or more further enzymes. All enzymes which can develop catalytic activity in the agent as contemplated herein, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase or a lipase, and mixtures thereof, can preferably be used as further enzymes. Further enzymes are contained in the agent advantageously in an amount of from about $1\times10^{-8}$ to about 5 wt. % in each case, based on the active protein. Each further enzyme is contained in agents as contemplated herein in an amount of, in order of increasing preference, from about $1\times10^{-7}$ to about 3 wt. %, from about 0.00001 to about 1 wt. %, from about 0.00005 to about 0.5 wt. %, from about 0.0001 to about 0.1 wt. %, and most particularly preferably from about 0.0001 to about 0.05 wt. %, based on the active protein. The enzymes particularly preferably have synergistic cleaning performances with respect to particular stains or marks, i.e. the enzymes contained in the agent composition assist one another in terms of the cleaning performance thereof. Very particularly preferably, such synergy exists between the protease contained as contemplated herein and a further enzyme of an agent as contemplated herein, in particular between the stated protease and an amylase and/or a lipase and/or a mannanase and/or a cellulase and/or a pectinase. Synergistic effects can occur not only between different enzymes, but also between one or more enzymes and other ingredients of the agent as contemplated herein.

The present disclosure further relates to a method for cleaning textiles or hard surfaces, exemplified in that an agent as contemplated herein is used in at least one method step, or in that a protease as contemplated herein becomes catalytically active in at least one method step, in particular such that the protease is used in an amount of from about 40 μg to about 4 g, preferably from about 50 μg to about 3 g, particularly preferably from about 100 μg to about 2 g, and very particularly preferably from about 200 μg to about 1 g.

In various embodiments, the above-described method is distinguished in that the protease is used at a temperature of from about 0 to about 100° C., preferably from about 0 to about 60° C., more preferably from about 20 to about 50° C., and most preferably at a temperature of approximately 40° C.

These embodiments include both manual and automatic methods, automatic methods being preferred. Methods for cleaning textiles are generally distinguished in that various substances that have a cleaning effect are applied to the item to be cleaned in a plurality of method steps and washed off after the contact time, or in that the item to be cleaned is treated with a washing agent or a solution or dilution of this agent in some other way. The same applies to methods for cleaning all materials other than textiles, in particular hard surfaces. All conceivable washing or cleaning methods can be enhanced in at least one of the method steps by the use of a washing or cleaning agent as contemplated herein or a protease as contemplated herein, and then constitute embodiments of the present disclosure. All elements, subjects and embodiments that are described for proteases as contemplated herein and agents that contain them can also be applied to this subject of the present disclosure. Therefore, at this juncture, reference is explicitly made to the disclosure at the corresponding point when it was indicated that this disclosure also applies to the above methods as contemplated herein.

Since proteases as contemplated herein naturally already have hydrolytic activity and these also develop in media that otherwise have no cleaning force, such as in simple buffers, an individual and/or the only step of a method of this kind can include bringing a protease as contemplated herein into contact with the stain as the only component that has a cleaning effect, preferably in a buffer solution or in water. This constitutes a further embodiment of this subject of the present disclosure.

Methods for treating textile raw materials or for textile care in which a protease as contemplated herein becomes active in at least one method step also constitute alternative embodiments of this subject of the present disclosure. Of such methods, methods for textile raw materials, fibers or textiles having natural components are preferred, and very particularly for those containing wool or silk.

Finally, the present disclosure further relates to the use of the proteases described herein in washing or cleaning agents, for example as described above, for (improved) removal of fat-containing stains, for example from textiles or hard surfaces.

All elements, subjects and embodiments that are described for proteases as contemplated herein and agents that contain them can also be applied to this subject of the present disclosure. Therefore, at this juncture, reference is explicitly made to the disclosure at the corresponding point when it was indicated that this disclosure also applies to the above use as contemplated herein.

EXAMPLES

All working steps involving molecular biology followed standard methods, as specified, for example, in the manual by Fritsch, Sambrook and Maniatis "Molecular cloning: a laboratory manual", Cold Spring Harbour Laboratory Press, New York, 1989, or comparable relevant pieces of work. Enzymes and kits were used according to the manufacturer's instructions in each case.

Example 1

Sequence of Purafact Prime (SEQ ID NO:1) and a Variant (SEQ ID NO:2) thereof

The comparison of the sequences of SEQ ID NO:1 (reference) and SEQ ID NO:2 (mutant) showed that the mutant sequence was 97% identical to the sequence of SEQ ID NO:1. The following mutations were present with respect to the sequence of SEQ ID NO:1: S24G, S33T, S53G, S78N, S101N, G128A and L217Q.

Example 2

Determining the Activity of the Protease

The proteolytic activity was determined by employing a discontinuous assay using casein as the substrate. The end concentrations of the substrate solution were 12 mg·ml$^{-1}$ casein (prepared according to Hammarsten; Merck, Darmstadt, #2242) and 30 mM tris in synthetic tap water. Synthetic tap water is a solution of 0.029% (w/v) $CaCl_2 \cdot 2H_2O$, 0.014% (w/v) $MgCl_2 \cdot 6H_2O$ and 0.021% (w/v) $NaHCO_3$ having a hardness of 15°dH (German degree of hardness). The substrate solution was heated to 70° C. and the pH was set at 8.5 at 50° C. using 0.1 N NaOH. The protease solution was prepared using 2% (w/v) water-free pentasodium phosphate in synthetic tap water, which was adjusted to pH 8.5 using hydrochloric acid. 200 μl of the enzyme solution was added to 600 μl casein substrate solution. The mixture was incubated at 50° C. for 15 minutes. The reaction was brought to an end by adding 600 μl 0.44 M trichloroacetic acid (TCA) and 0.22 M sodium acetate in 3% (v/v) glacial acetic acid. After cooling to form ice for 15 minutes, the TCA-insoluble protein was removed by centrifugation, an aliquot of 900 μl was mixed with 300 μl 2N NaOH, and the extinction of this mixture, which contains TCA-soluble peptide, was measured at 290 nm. Control values were obtained by adding 600 μl TCA solution to 600 μl of the casein solution, followed by 200 μl enzyme solution. A protease solution which has an extinction change of 0.500 OD at 290 nm under the conditions of this assay had an activity of 10 HPU per ml.

Example 3

Mini Washing Test

The mini washing test was carried out by employing the fermentation supernatant of the prepared protease. The reference enzymes were a technical sample.

Conditions: 40° C., 16° dH water, 1 h
Enzyme concentration: washing was carried out in an AEP-equal manner (1.7 μg/mL)
Stains:
C-05 (blood, milk, ink)
C-03 (chocolate milk and carbon black)
EMPA 112 (cocoa)
C-S-38 (egg yolk with pigment, aged)
PC-10 (peanut, pigment, milk)
Method:
A woven fabric blank (diameter=10 mm) was placed in a microtiter plate, washing liquor was preheated to 40° C., and the end concentration was 4.52 g/L in 16°dH water. The liquor and enzyme were put on the stain and incubated for 1 h at 40° C. and 600 rpm, then the stain was rinsed several times with clear water and left to dry, and the lightness was determined using a color measurement device.

The lighter the woven fabric, the better the cleaning performance. What was measured in this case was the L value=lightness, and the higher the value the lighter the stain. Washing was carried out using a conventional liquid washing agent without any enzymes (LSPA+).
Sample 1: washing agent as benchmark
Sample 2: reference protease 1 (wild-type BLAP with mutations S3T, V4I, V193M, V199I and L211D in the numbering according to BLAP)
Sample 3: reference protease 2 (subtilisin Carlsberg from *Bacillus licheniformis* ATCC 53926 strain) Sample 4: protease as contemplated herein (SEQ ID NO:2)

The sum of the differences in the L value is given in the table. In this table, the performance of the washing agent (sample 1) has not been included with the samples containing a protease.

TABLE 1

|  | Sample 2 | Sample 3 | Sample 4 |
|---|---|---|---|
| Σ Δ L on five stains | 34.0 | 29.9 | 40.0 |

As is clear from table 1, the mutant has improved washing performance on the five selected stains by comparison with the reference enzymes.

Example 4

Washing agent matrix used:

| Chemical name | wt. % active substance in the raw material | wt. % active substance in the formulation |
|---|---|---|
| demineralized water | 100 | remainder |
| alkylbenzene sulfonic acid | 96 | 4.40 |
| other anionic surfactants | 70 | 5.60 |
| C12-C18 fatty acid Na salt | 30 | 2.40 |
| non-ionic surfactants | 100 | 4.40 |
| phosphonates | 40 | 0.20 |
| citric acid | 100 | 1.43 |
| NaOH | 50 | 0.95 |
| defoamers | t.q. | 0.01 |
| glycerol | 100 | 2.00 |
| preservatives | 100 | 0.08 |
| ethanol | 93 | 1.00 | without optical brighteners, perfume, dye and enzymes.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

---

The invention claimed is:

1. A polypeptide comprising a sequence derived from SEQ ID NO: 1, wherein the sequence consists of the amino-acid substitutions S24G, S33T, S53G, S78N, S101N, G128A and L217Q of SEQ ID NO: 1.

* * * * *